United States Patent [19]

Felder et al.

[11] Patent Number: 4,588,574

[45] Date of Patent: May 13, 1986

[54] PROCESS FOR THE PREPARATION OF BARIUM SULFATE OF INCREASED FLOWABILITY AND DENSITY, SUITABLE AS A RADIO-OPAQUE COMPONENT IN RADIOGRAPHIC CONTRAST AGENTS, PRODUCT OBTAINED ACCORDING TO THIS PROCESS AND THE RADIOGRAPHIC CONTRAST AGENT PRODUCED THEREFROM

[75] Inventors: Ernst Felder, Vitale, Switzerland; Maria Zingales, deceased, late of Milan, Italy, by Martinis Marchi Jellicich Maria Sonia, administrator

[73] Assignee: Bracco Industria Chimica S.p.A., Italy

[21] Appl. No.: 636,399

[22] Filed: Jul. 31, 1984

[30] Foreign Application Priority Data

Aug. 4, 1983 [IT] Italy ............................... 22425 A/83

[51] Int. Cl.$^4$ ............................................. C01F 11/46
[52] U.S. Cl. ........................................ 423/554; 424/4; 424/5; 429/1; 429/19
[58] Field of Search ..................... 424/4, 5; 423/554; 419/1, 19

[56] References Cited

U.S. PATENT DOCUMENTS

| 2,039,432 | 5/1936 | McCallum | 423/554 |
| 2,056,929 | 10/1936 | Moore | 423/554 |
| 2,159,909 | 5/1939 | Price | 423/554 |
| 2,509,585 | 5/1950 | Brown | 423/554 |
| 3,689,630 | 9/1972 | Kikuchi et al. | 424/4 |

FOREIGN PATENT DOCUMENTS

| 1050235 | 3/1979 | Canada | 423/554 |
| 2134341 | 1/1973 | Fed. Rep. of Germany | 424/4 |
| 2703600 | 8/1978 | Fed. Rep. of Germany | 424/4 |
| 3203479 | 8/1983 | Fed. Rep. of Germany | 423/554 |

*Primary Examiner*—John F. Niebling
*Assistant Examiner*—Terryence Chapman
*Attorney, Agent, or Firm*—Toren, McGeady, Stanger, Goldberg & Kiel

[57] ABSTRACT

Barium sulfate suitable for the preparation of radiographic contrast agents of increased flowability and density is obtained by a high temperature treatment at 700° to 1,200° C. and preferably at 800° to 1,000° C. The barium sulfate so sintered is distinguished by a bulk density of 2.5 to 3 g/ml and its aqueous suspension, containing 200 g of barium sulfate per 100 ml, is distinguished by a viscosity of no more than 1,000 mPas. Radiographic contrast agents containing at least 200 g of sintered barium sulfate per 100 ml are outstandingly suitable for the difficult double contrast visualization of the stomach and gastric mucosa.

14 Claims, No Drawings

PROCESS FOR THE PREPARATION OF BARIUM SULFATE OF INCREASED FLOWABILITY AND DENSITY, SUITABLE AS A RADIO-OPAQUE COMPONENT IN RADIOGRAPHIC CONTRAST AGENTS, PRODUCT OBTAINED ACCORDING TO THIS PROCESS AND THE RADIOGRAPHIC CONTRAST AGENT PRODUCED THEREFROM

BACKGROUND OF THE INVENTION

1. Field of the Invention

The present invention relates to a process for the preparation of sintered barium sulfate which is suitable for the preparation of radiographic contrast agents. The invention also includes the barium sulfate obtained according to this process, which has an increased bulk density as compared to that of the starting material and whose aqueous suspensions have a greatly increased flowability, as well as the correspondingly improved radiographic contrast material produced from this sintered material.

2. Description of the Prior Art

Barium sulfate continues to be the most important radio-opaque component in radiographic contrast materials used for visualizing the gastrointestinal tract. Numerous new barium sulfate preparations and corresponding patents confirm the unsurpassed basic suitability of this radio-opaque compound.

For practical applications, barium sulfate preparations are desired which combine the highest radiation absorption with good flowability so that the preparations penetrate into all parts and folds of the body, and adequate shadow density is obtained even when the layer is thin.

German Offenlegungsschrift No. 2,703,600 of 8/3/78 (Fredi Fischer) is exemplary of the state of the art for generally applicable preparations. This patent discloses that barium sulfate, suitable for use as a radiographic contrast agent, should have a bulk density of at least 1.2 g/ml and preferably of 1.6 to 1.7 g/ml.

Radiographic contrast agents which are suitable for the double contrast visualization of the stomach and gastric mucosa must meet even stricter requirements in respect to density and flowability. Double contrast visualization is a method developed in recent years for detecting lesions of the gastric mucosa which usually represent the first stage of a carcinosis of the gastric wall (R. E. Miller and J. Skucas, Radiographic Contrast Agents, University Park Press 1977, pages 144–146). The prospects of treating stomach cancer can be improved dramatically through the early identification of such lesions. As is well known, advanced stomach cancer which can also be identified by conventional contrasting agents, has a very poor prognosis (I. Laufer et al, Diagnostic Radiology, Vol. 115, June 1975, pages 569–575).

In the double contrast visualization of the stomach or the gastric mucosa, for example, the stomach is filled tightly with carbon dioxide which is given off by carbonates administered to the stomach. A relatively small amount of a highly concentrated barium sulfate suspension of the lowest possible viscosity is now introduced. If the barium sulfate suspension is sufficiently flowable, it spreads over the extended gastric wall with all its recesses and fine structures, while the gas itself acts as a negative contrasting agent. A fine layer of barium sulfate is to form on the folds of the mucous membrane in a way that it becomes visible in the double contrast X-ray picture, provided the barium sulfate suspension is sufficiently concentrated. The higher the concentration of the barium sulfate suspension, the thinner are the layers which can be identified in the X-ray picture. The more flowable the suspension, the better is the penetration into the finest interstices and folds and the more differentiated are the structures which become visible (I. Laufer, Diagnostic Radiology, Vol. 117, December 1975, pages 513–518).

By using double contrast visualization, it was possible to improve by far the proportion of carcinomas found. Under optimum conditions, carcinomas of a few millimeters to only 1 millimeter in diameter can be identified. The highest possible concentration and, at the same time, very good flowability of the barium sulfate suspension used over a wide pH range, are thus the primary absolute requirement for good double contrast visualizations. The gastric juice, whose pH can fluctuate over a wide range, should not cause any flocculation of the contrasting agent. (R. E. Miller and J. Skucas, loc. cit.)

The double contrast visualization of the intestinal mucosa with which relatively slight typical changes in the mucosa relief, and therefore carcinoma in the early stages, can be diagnosed, is based on a similar principle.

Barium sulfate formulations suitable for the double contrast visualization of the stomach or the gastric mucosa should contain at least 200, and preferably 250 g, of barium sulfate per 100 ml. Formulations of the required high concentration which are adequately flowable can usually not be prepared from conventional commercially available precipitated barium sulfate powders conforming to the requirements of the pharmacopeia. This is so whether coarsely or very finely milled preparations are used for this purpose (cf., for example, W. B. James, British Journal of Radiology, 51, 1978, pages 1020–1022). Certain mineral barium sulfates from South Australia, for example, after being milled to particle sizes of about 1 to 30 μm, produce highly concentrated suspensions of sufficient flowability. Unfortunately, such baryta generally do not satisfy the purity requirements of the pharmacopeias. They usually contain too high a concentration of heavy metals (R. E. Miller and J. Skucas, loc. cit.).

Therefore, an acute need exists for barium sulfate of high bulk density whose highly concentrated aqueous suspensions have good flowability.

SUMMARY OF THE INVENTION

We have discovered that the bulk density of barium sulfate as well as the flowability of aqueous suspensions of the same, can be substantially improved, if barium sulfate produced by precipitation or milled barium sulfate, is subjected to a high temperature treatment. In so doing, the barium sulfate is sintered, which increases the flowability, decreases the distances between the particles, and therefore increases the packing and the density.

The high temperature treatment causes sintering whereby the particles grow into one another, the edges and corners of the particles are fused and the surface is smoothed out. The frictional resistance between the particles is thereby reduced and the bulk density increased.

Preparations of the highest bulk density and adequate flowability may be obtained from the barium sulfate obtained by the high temperature treatment, after the usual additives have been added. Through the high temperature treatment, especially of fine-grained barium sulfates of synthetic origin, products are obtained which have a bulk density of 2.5 to 3 g/ml and a viscosity of less than 1,000 mPas (1 mPas corresponds to 1 centipoise) at a concentration of 200 g per 100 ml.

The flowability of the suspensions remains practically constant over a wide pH range of about 6 to 1.2. The entry of the corresponding suspension into the stomach therefore causes no flocculation.

These are very significant advantages over the best of the known preparations which contain precipitated and therefore pure barium sulfate and which are generally less suitable for the double contrast visualization of the gastric mucosa. Although improved properties are urgently required especially for precipitated, that is, synthetic barium sulfate, mineral barium sulfates (baryta) may also be improved by the high-temperature treatment.

DESCRIPTION OF THE PREFERRED EMBODIMENT

In order to achieve this effect, heating to 700° to 1200° C. is required. For the purpose of retarding partial thermolysis of the barium sulfate, especially in the upper region of said temperature interval, the barium sulfate, before being heated, can be impregnated with a sulfate, such as, a sulfate which is volatile or decomposes at elevated temperatures (ammonium sulfate, for example), or with an amine sulfate or an alkali sulfate (sodium or potassium sulfate) or with magnesium or calcium sulfate.

When a sulfate which is volatile or decomposes at elevated temperatures is used for the impregnation, the high temperature treatment leads directly to a product which meets the requirements of the U.S. Pharmacopeia XX without further treatment and which can be used directly for the preparation of radiographic contrast agents. When alkali sulfates or magnesium or calcium sulfates are used, the sintered barium sulfate obtained after the high temperature treatment must be washed with water.

If impregnation with a sulfate is dispensed with, extensive washing, possibly with hydrochloric acid to remove traces of barium oxide formed and subsequent washing with water is appropriate for safety reasons. The products obtained meet the requirements of the U.S. Pharmacopeia XX.

More specifically, the inventive process for producing barium sulfate which has increased flowability and bulk density and is suitable as opaque component in radiographic contrast agents, comprises subjecting precipitated or mineral barium sulfate to a high temperature treatment. The high temperature treatment is carried out at 700° to 1,200° C. The preferred temperature range is 800° to 1,000° C. In a preferred embodiment of the inventive process, the barium sulfate is impregnated, before the high temperature treatment, with a sulfate which is volatile or decomposes at elevated temperatures, an alkali sulfate or with magnesium or calcium sulfate. Particularly preferred is the impregnation of pure barium sulfate with an ammonium sulfate and then subjecting the impregnated barium sulfate to a high temperature treatment at 800° to 1,000° C.

The invention also provides a sintered barium sulfate of high flowability and bulk density suitable for the preparation of radiographic contrast agents. The barium sulfate of the invention has a bulk density of at least 2.5 g/ml and its aqueous suspension has a viscosity of no more than 1,000 mPas at a concentration of 200 g per 100 ml.

In addition, the invention provides a radiographic contrasting agent of high flowability and shadow density which contains an aqueous suspension of the above-described sintered barium sulfate. The radiographic contrast agent is characterized by the fact that it contains barium sulfate which has a bulk density of at least 2.5 g/ml, was sintered at 700° to 1,200° C. and whose aqueous suspension has a viscosity of not more than 1,000 mPas at a concentration of 200 g/100 ml.

Such radiographic contrast agents are suitable for the double contrast visualization of the stomach and the gastric mucosa and are characterized by the fact that they contain at least 200 g per 100 ml of barium sulfate which has been sintered by a high temperature treatment as well as up to 3 weight percent of auxiliary materials for improving the taste, the flow behavior and the stability and for decreasing the interfacial tension of the composition.

As the starting material for the inventive process, commercially available barium sulfate which meets the requirements of the U.S. Pharmacopeia XX, may be used. The particle size of the starting material which increases during the high-temperature treatment, should be as small as possible, preferably from about 1 to 30 μm, and most preferably from 1 to 5 μm.

The following examples illustrate the invention. The preparations obtained by the high temperature treatment were compared in respect to their viscosity, bulk density, particle size distribution and their appearance at 1,000×, 5,000×, and 50,000× magnification.

EXAMPLES OF THE HIGH TEMPERATURE TREATMENT OF BARIUM SULFATE AND COMPARISON OF THE PREPARATIONS OBTAINED

Example 1

An aqueous barium sulfate suspension containing 214% (g/v) barium sulfate (particle size 8 to 10 μm) is mixed with sodium hydroxide until the concentration of the latter corresponds to 8.5% (g/v). The suspension obtained is predried for 3 hours at 80° C. and then held in a muffle furnace at 800° C. for 90 minutes.

After cooling, the barium sulfate is comminuted, milled and screened through a screen with a mesh width of 396 μm. The screened product is mixed with 10% hydrochloric acid to give a suspension of 45% (g/v) of barium sulfate and stirred for 90 minutes at 80° C. After cooling, the barium sulfate is filtered off and washed with water until chloride ions can no longer be detected in the wash water. The washed barium sulfate is dried at 80° C. and screened. The barium sulfate obtained corresponds to the requirements of the U.S. Pharmacopeia XX.

Example 2

Barium sulfate of a particle size of 1 to 3 μm is moistened with 0.5% aqueous ammonium sulfate. The paste obtained is heated for 1 hour in a muffle furnace at 900° C. After cooling, the product is comminuted, milled and screened through a screen with a mesh width of 138 μm. The barium sulfate obtained meets the requirements of U.S.P. XX.

Example 3

Barium sulfate powder of a particle size of 1 to 3 μm is heated for 90 minutes in a muffle furnace at 900° C. After cooling, the product is comminuted, milled and screened. An aqueous suspension of the product so obtained is stirred for 90 minutes at 80° C., subsequently filtered and washed with water until barium ions can no longer be detected in the filtrate with sulfuric acid. The barium sulfate obtained is washed and screened. It meets the requirements of U.S.P. XX.

Properties of the Products Obtained

The following characteristic data was determined: viscosity, bulk density and appearance under the microscope.

The viscosity of aqueous suspensions of barium sulfate was determined according to the American National Standard Method DM 1200 of the American Society for Testing Materials (ASTM) by means of a No. 4 FORD viscosity cup. According to this method, the efflux time in seconds, taken by a suspension to flow from the standardized beaker with a specified opening, is measured.

TABLE 1

| BaSO$_4$ Particle Size Treatment | Viscosity at 25° C. Concentration in % (g/v) | Time in Seconds to Flow from #4 FORD Cup pH ~ 7 | pH 1.2 |
|---|---|---|---|
| 8–10 μm untreated | 200* | semisolid paste | semisolid paste |
| according to Example 1 | 250 | 30" | 30" |
| 1–3 μm untreated | 90* | semisolid paste | semisolid paste |
| according to Example 2 | 250 | 31" | 25" |
| Example 3 | 250 | 28" | 20" |

*highest possible concentration for a stirrable suspension

Viscosity was determined with a Brookfield rotation viscosimeter.

TABLE 2

| Concentration of BaSO$_4$ in % (g/v) | Viscosity in Millipascal Seconds (1 mPas corresponds to 1 centipoise (cP)) According to | | | |
|---|---|---|---|---|
| | Untreated | Example 1 | Example 2 | Example 3 |
| Particle size 8–10 μm | | | | |
| 150 | 660 | 100 | | |
| 200 | >>2000* | 450 | | |
| 250 | | 1800 | | |
| Particle size 1–3 μm | | | | |
| 50 | 600 | | | |
| 100 | >>2000** | | <50 | 50 |
| 150 | | | 140 | 160 |
| 200 | | | 400 | 650 |
| 250 | | | 2200 | >2000*** |

*180% (g/v) BaSO$_4$ = 1900 mPas
**80% (g/v) BaSO$_4$ = 1500 mPas
***230% (g/v) BaSO$_4$ = 1700 mPas

Bulk Density (Powder Density) of Barium Sulfate Powders

TABLE 3

| Particle Size in μm | Bulk Density in g/ml (according to DIN 53194) | | | |
|---|---|---|---|---|
| | untreated | Example 1 | Example 2 | Example 3 |
| 8–10 | 2 | 2.71 | | |
| 1–3 | 1.05 | | 2.53 | 2.71 |

Particle Size Distribution

TABLE 4

| Size in μm | Particle Size Distribution in % (g/g) | | | | |
|---|---|---|---|---|---|
| | untr. 8–10 μm | Example 1 | untr. 1–3 μm | Example 2 | Example 3 |
| 20 | 3.7 | 20 | | 3 | 27.61 |
| 20–15 | 9.6 | 29.8 | | 1.6 | 15.28 |
| 15–10 | 28.1 | 27.4 | | 3.1 | 18.92 |
| 10–5 | 34.7 | 15.4 | | 19.1 | 22.19 |
| 5–3 | 10.1 | 3.6 | 2.4 | 38 | 8.93 |
| 3 | 13.7 | 3.7 | 97.6 | 35.2 | 7.06 |

Appearance

The appearance of the barium sulfate particles was evaluated at 1,000×, 5,000× and 50,000× magnification. An increase in the number of larger particles was noted which undoubtedly occurred due to the sintering together of small crystal chips. Moreover, it is noted that the edges and corners were rounded off and the surfaces were smoothed out to some degree.

The very considerable improvement in barium sulfates with respect to their suitability as radio-opaque components in radiographic contrast agents is clearly expressed by the preceding data. The bulk density is increased and the viscosity of aqueous suspensions is greatly reduced.

Examples 4–7

Barium sulfate powders of particle sizes of 1 to 3 μm are moistened with 1% aqueous solution of
4. bis(dimethylammonium) sulfate
5. sodium sulfate
6. potassium sulfate, or
7. magnesium sulfate.

The pastes thus obtained are dried and heated for 2 hour in a muffle furnace at 900° C. After cooling, the product is comminuted, milled, screened and extensively washed with water. In Example 4, it is not necessary to wash with water.

Example 8

Barium sulfate powder having a particle size of 1–3μm is mixed with a 1% suspension of calcium sulfate into a homogeneous stiff paste and heated at 900° C. for one hour. After cooling, the treated material is worked up as described in Example 3. The product contains traces of calcium sulfate.

Examples 9–17

Barium sulfate powders of a particle size of 1–3 μm are heated in a muffle furnace to 600°, 700°, 750°, 800° and 1050° C. After cooling, the product obtained is, in each case, comminuted, milled, screened and worked up as described in Example 3. Table 5 shows the specific conditions of the high temperature treatment, the bulk density of the products obtained, as well as the flowability of their aqueous suspensions containing 250 g barium sulfate/100 ml in the pH range resulting directly (pH 4–7) and after acidification to a pH of 1.2 (pH of the gastric juices).

TABLE 5

Properties of the Products Obtained

| High Temperature Treatment | | Bulk Density (DIN 53194) | Viscosity with # 4 FORD Cup | |
|---|---|---|---|---|
| Temperature °C. | Time in Hours | | Efflux Time in Seconds | |
| | | | pH 4–7 | pH 1.2 |
| 9. 600 | 4 | 1.15 | paste | paste |
| 10. 700 | 2 | 2.30 | 16 | 16 |
| 11. 750 | 0.5 | 2.12 | 16 | 16 |
| 12. 750 | 2 | 2.57 | 16 | 16 |
| 13. 750 | 4 | 2.57 | 16 | 16 |
| 14. 800 | 0.5 | 2.57 | 16 | 16 |
| 15. 800 | 1 | 2.57 | 16 | 16 |
| 16. 800 | 2 | 2.65 | 16 | 16 |
| 17. 1050 | 1 | 2.98 | 16 | 14 |

As can be seen, heating to 600° C. is not sufficient. Adequate sintering is not achieved even after 4 hours. At 800° C., a heating period of 0.5 hours is already sufficient for obtaining a dense, readily flowable product. Denser products with the high bulk density of approximately 3 are obtained by heating to higher temperatures.

Examples of Formulating Radiographic Contrast Agents

Dry preparations which can be mixed with a little water to form a stable suspension, or preferably, finished, aqueous barium sulfate suspensions are used in practice. This calls for the addition of auxiliaries for improving the taste, the flow behavior and the stability and for decreasing the interfacial tension. The total concentration of the auxiliaries should not exceed 3% (g/g) so as not to excessively dilute the contrast agent.

1. Contrast Agent Powder for Mixing with Water

In the following, three formulations for dry preparations are given. These preparations are distributed in bags, bottles or cans. For administration to patients, the dry preparations are mixed with 45 ml of water to form 100 ml of a ready-for-use, readily flowable suspension which is suitable for the double contrast visualization of the stomach or the gastric mucosa.

| Formulation 1 | |
|---|---|
| Barium sulfate prepared according to Example 1 | 250 g |
| Sorbitol (D-sorbit) | 2.94 g |
| Simethicone $(CH_3)_3Si[OSi(CH_3)_2]_nCH_3$* | 500 mg |
| Hydrolized carrageenan | 300 mg |
| Strawberry flavor | 180 mg |
| Vanilla flavor | 50 mg |
| Citric acid | 20 mg |
| Sodium salt of saccharin | 5.9 mg |

*Merck Index, 9th Ed. No. 8374

| Formulation 2 | |
|---|---|
| Barium sulfate prepared according to Example 2 | 250 g |
| Sorbitol (D-sorbit) | 2.94 g |
| Hydrolized carrageenan | 1.1 g |
| Simethicone (polydimethylsiloxane, stabilized with silicon dioxide) | 500 mg |
| Sodium polyphosphate | 220 mg |
| Strawberry flavor | 180 mg |
| Sodium sulfate | 147 mg |
| Vanilla flavor | 50 mg |
| Citric acid | 20 mg |
| Sodium salt of saccharin | 5.9 mg |

| Formulation 3 | |
|---|---|
| Barium sulfate prepared according to Example 2 | 250 g |
| Sorbitol (D-sorbit) | 2.94 g |
| Hydrolized carrageenan | 730 mg |
| Simethicone | 500 mg |
| Sodium sulfate | 370 mg |
| Cherry flavor | 180 mg |
| Sodium dextran sulfate (mol wt. ~ 5,000) | 160 mg |
| Vanilla flavor | 50 mg |
| Citric acid | 20 mg |
| Aspartame (α-L-aspartyl-L-phenylalanine methyl ester) | 18 mg |

The viscosities of the suspensions obtained with formulations 1, 2, and 3 were measured as such and after acidification to a pH of 1.2 (pH of the gastric juices) by the FORD method with cup No. 4.

| Formulation | Viscosity in Seconds | |
|---|---|---|
| | pH ~ 5 | pH 1.2 |
| 1 | 21 (pH 4.8) | 21 |
| 2 | 18 (pH 4.9) | 19 |
| 3 | 18 (pH 5.5) | 19 |

If the barium sulfate in Formulations 1, 2 and 3 is replaced by unsintered barium sulfate of the same source, a paste which is not free flowing and whose viscosity cannot be determined with the FORD cup is obtained in all three cases on mixing with 45 ml of water.

2. Ready-for-Use Radiographic Contrast Agent Suspension

| Barium sulfate prepared according to Example 2 | 200 g |
|---|---|
| Sorbitol (D-sorbit) | 2.94 g |
| Hydrolyzed carrageenan | 730 mg |
| Simethicone (polydimethylsiloxane + small amount silicon dioxide) | 500 mg |
| Sodium sulfate | 370 mg |
| Strawberry flavor | 180 mg |
| Sodium dextran sulfate (mol. weight ~ 5000) | 160 mg |
| Sodium benzoate | 118 mg |
| Vanilla flavor | 50 mg |
| Citric acid | 20 mg |
| Sodium salt of saccharin | 5.9 mg |
| Purified water | 48 ml |

The preparation is mixed and filled into plastic bags, bottles or cans.

The preparation shows good flowability. The viscosity, determined with a FORD cup No. 4 is:

| Preparation | pH 5.5. | 16 sec. efflux time |
|---|---|---|
| Preparation acidified to | pH 1.2 | 16 sec. efflux time |

Comparison with Unsintered Barium Sulfate

With the same formulation but using barium sulfate which had not been sintered, a paste was obtained which was not free flowing.

3. Further Formulation Examples of Ready-For-Use Barium Sulfate Preparations Which Are Suitable for the Double Contrast Visualization of the Stomach Composition of the Preparations:

Barium sulfate (250 g), produced according to the respective example as listed in Table 6, is mixed with 3 g of flavoring materials and sweeteners, a polysaccharide or salt and with the amount of water as shown, and worked up into a homogeneous suspension. The viscosities of the suspensions obtained as such, and after acidification to pH 1.2 (the pH of the gastric juices), were determined by the method of FORD with a No. 4 cup. Efflux times in seconds (sec.)

TABLE 6

| Preparation | Example No. | Polysaccharide or Salt | Water g | Viscosity in sec. pH ~ 5 | pH 1.2 |
|---|---|---|---|---|---|
| A | 2 | Na cellulose sulfate | 100 mg | 47.5 | 19 | 17 |
| B | 3 | Na cellulose sulfate | 100 mg | 45 | 23 (pH 5.7) | 18 |
| C | 2 | Na dextran sulfate (average mol. weight 5,000) | 500 mg | 47.5 | 15 | 13 |
| D | 3 | Na dextran sulfate | 500 mg | 45 | 14 (pH 5.2) | 14 |
| E | 2 | Hydrolyzed carrageenan | 500 mg | 47.5 | 16 (ph 4.5) | 15 |
| F | 3 | Hydrolyzed carrageenan | 500 mg | 45 | 18 (pH 4.7) | 16 |
| G | 2 | Sodium citrate | 370 mg | 47.5 | 15 (pH 6.25) | 20 |
| H | 3 | Sodium citrate | 370 mg | 45 | 16 (pH 6.5) | 19 |
| I | 1 | Sodium citrate | 370 mg | 45.6 | 24 (pH 6.5) | 26 |
| K | 2 | Na pyrophosphate | 370 mg | 47.5 | 16 (pH 7) | 26 |
| L | 3 | Na pyrophosphate | 370 mg | 45 | 19 (pH 8.4) | 27 |
| M | 2 | Na dioctyl sulfosuccinate | 370 mg | 47.5 | 17 (pH 4.8) | 14 |
| N | 3 | Na dioctyl sulfosuccinate | 370 mg | 45 | 24 (pH 5.8) | 12 |
| O | 1 | Na dioctyl sulfosuccinate | 370 mg | 45.6 | 31 (pH 7.0) | 26 |

In the formulation examples also, the comparison of preparations which were prepared from barium sulfate sintered by a high temperature treatment with preparations of otherwise identical composition, which were obtained from the corresponding barium sulfate which had not been sintered, shows that only sintered barium sulfate permits the preparation of highly concentrated and at the same time flowable radiographic contrast agents.

High concentration and good flowability are the two main requirements for a radiographic contrast agent which is suitable for the double contrast visualization of the stomach or gastric mucosa. Due to adequate opacity even of thin layers and the ability to penetrate into the finest folds of the mucous membrane, relief visualizations of the mucous membrane can be produced which permit the identification of stomach cancer in the early stages with a high degree of reliability. The poor prognosis of stomach cancer can be improved by this early identification.

We claim:

1. A process for the treatment of barium sulfate comprising subjecting precipitated or mineral barium sulfate to a high temperature treatment for a time and temperature sufficient to increase the flowability and bulk density of the barium sulfate to render it suitable for use as a radio-opaque component in radiographic contrast agents.

2. The process of claim 1 wherein the heat treatment is sufficient to sinter the barium sulfate.

3. The process of claim 1 wherein the heat treatment is carried out a temperature from 700° to 1200° C.

4. The process of claim 3 wherein the temperature is from 800° to 1,000° C.

5. The process of claim 1, 2, 3 or 4 wherein the barium sulfate is impregnated with a sulfate which is volatile or decomposable at elevated temperatures, an alkali sulfate or with magnesium or calcium sulfate, before the high temperature treatment is carried out.

6. The process of claim 1, 2, 3 or 4 wherein the heat treatment is sufficient to produce barium sulfate having a bulk density of at least 2.5 g/ml and whose suspension in pure water at a concentration of 200 g per 100 ml has a viscosity of not more than 1,000 mPas.

7. The process of claim 1, 2, 3 or 4 wherein the barium sulfate is impregnated with a sulfate which is volatile or decomposable at elevated temperatures, an alkali sulfate or with magnesium or calcium sulfate, before the high temperature treatment is carried out and wherein the heat treatment is sufficient to produce barium sulfate having a bulk density of at least 2.5 g/ml and whose suspension in pure water at a concentration of 200 g per 100 ml has a viscosity of not more than 1,000 mPas.

8. The process of claim 1, 2, 3 or 4, wherein the particle size of the barium sulfate starting material is in the range from about 1 to 30 μm.

9. Barium sulfate produced by the process of claim 1, 2, 3 or 4 having a bulk bensity of 2.30 to 2.98 g/ml.

10. The process of claim 1 wherein pure barium sulfate is impregnated with an ammonium sulfate and then subjected to a high temperature treatment at 800° to 1,000° C.

11. Barium sulfate produced by the process of claim 6 having bulk density of 2.53 g/ml and a viscosity of 400 mPas at a concentration of 200 g per 100 ml.

12. Barium sulfate having a bulk density of at least 2.5 g/ml and whose suspension in pure water has a viscosity not greater than 1,000 mPas at a concentration of 200 g per 100 ml.

13. In a radiographic contrast agent composition composed of a radio-opaque effective amount of barium sulfate and conventional additives, the improvement which comprises said barium sulfate having a bulk density of at least 2.5 g/ml and whose suspension in pure water has a viscosity not greater than 1,000 mPas at a concentration of 200 g per 100 ml.

14. The composition of claim 13 which contains at least 200 g per 100 ml of barium sulfate and up to 3 weight percent additives.

* * * * *